United States Patent [19]
Amagai et al.

[11] Patent Number: 5,807,975
[45] Date of Patent: Sep. 15, 1998

[54] ALKYL SULFIDE TYPE EPISULFIDE COMPOUND

[75] Inventors: Akikazu Amagai; Motoharu Takeuchi; Kenichi Takahashi, all of Tokyo, Japan

[73] Assignee: Mitsubishi Gas Chemical Company, Inc., Tokyo, Japan

[21] Appl. No.: 693,592

[22] Filed: Aug. 2, 1996

[30] Foreign Application Priority Data

Aug. 16, 1995 [JP] Japan .................................... 7-208799
Sep. 8, 1995 [JP] Japan .................................... 7-231283

[51] Int. Cl.$^6$ .................................................... C08G 75/00
[52] U.S. Cl. ........................ 528/373; 528/374; 528/375; 528/377; 523/427; 523/428; 359/642
[58] Field of Search ...................... 528/373, 374, 528/375, 377; 523/427, 428; 359/642

[56] References Cited

U.S. PATENT DOCUMENTS 3,378,522   4/1968  Martin .

FOREIGN PATENT DOCUMENTS 2 009 347   9/1970  Germany .
1 101 592   1/1968  United Kingdom .
1 252 717  11/1971  United Kingdom .

OTHER PUBLICATIONS

"Crosslinkage of collagen by polyglycidyl ethers" Tang et al. ASAIO J., 41(1), 72–8, 1995.

"Conversion products of bis (glycidylthio) ethers" Wirth et al. 1988.

C. Bonnans–Plaisance et al, "Preparation and polymerization of poly(ethylene oxide) macromonomers", Polymer Bulletin, vol. 34, No. 2, 1995, Berlin, pp. 141–147.

Chemical Abstracts, vol. 120, No. 21, 23 May 1994, Columbus, Ohio, Abstract No. 269968x, XP002021376 * abstract; RN: 108106–35–0, 154504–95–7, 154504–96–8 * of Izv. Nats. Akad. Nauk Resp. Kaz., Ser. Khim., No. 2, 1993, pp. 52–55, E.E. Ergozhin et al.

Patent Abstracts of Japan, vol. 15, No. 252 (C–0844), 26 Jun. 1991 of JP 03 081320 A (Mitsui Toatsu Chem Inc).

*Primary Examiner*—Duc Truong
*Attorney, Agent, or Firm*—Frishauf, Holtz, Goodman, Langer & Chick, P.C.

[57] ABSTRACT

An alkyl sulfide type episulfide compound represented by the following general formula (I) or (II) is herein disclosed:

$$CH_2CHCH_2S[(CH_2)_mS]_nCHCH_2 \quad (I)$$
with X bridging groups on each end $$(E_{PS}SCH_2CH_2S)_u-C-(CH_2SE_{PS})_y \quad (II)$$
with $[(CH_2)_vH]_k$ and $(CH_2SCH_2CH_2SE_{PS})_z$ substituents A material obtained by polymerizing/curing the above-mentioned compound is desirable as an optical material for various purposes, particularly a lens material for spectacles.

15 Claims, No Drawings

ALKYL SULFIDE TYPE EPISULFIDE COMPOUND

BACKGROUND OF THE INVENTION

1. Field of the Invention

The present invention relates to a novel alkyl sulfide type episulfide compound. More specifically, the present invention relates to a novel alkyl sulfide type episulfide compound which can suitably be used as an optical material for plastic lenses, prisms, optical fibers, information recording substrates, filters and the like, above all, a material for plastic spectacle lenses.

2. Description of the Related Arts

Plastic materials are lightweight, tough and easily dyeable, and for this reason, they have often been used as various optical materials, particularly spectacle lenses in recent years. As the performance of the optical materials, particularly the spectacle lenses, they are required to possess a low specific gravity, optical performances such as a high refractive index and a high Abbe's number, and physical performances such as a high heat resistance and a high strength. The high refractive index permits the lenses to be thinned, the high Abbe's number decreases the chromatic aberration of the lenses, and the high heat resistance and the high strength can facilitate the secondary processing of the lenses and they are also important from the viewpoints of safety and the like. Typical plastic materials at an early stage of conventional techniques in this field are materials obtained by polymerizing compounds such as diethylene glycol bisallyl carbonate, a combination of this bisallyl carbonate and diallyl phthalate, and various kinds of methacrylates. These plastic materials have a refractive index of about 1.5 to 1.55, so that the obtained lenses are thick, and in consequence, the lightweight properties are lost. Therefore, the materials having the high refractive index have been desired, and various investigations have been conducted with the intention of obtaining a refractive index of 1.6 or more. There have already been suggested a polymer of a methacrylate compound containing a chlorine atom or a bromine atom, and a thermosetting optical material having a urethane structure obtained by the reaction of a hydroxy compound containing the bromine atom with an isocyanate (Japanese Patent Application Laid-open No. 164615/1983 and the like). However, when the compound containing the chlorine atom or the bromine atom is used, the specific gravity of the obtained lenses is large, and also in this case, the lightweight properties are eventually lost. Thus, thermosetting optical materials having thiourethane structures obtained by the reaction of polythiol compounds with polyisocyanate compounds have been suggested in Japanese Patent Publication No. 58489/1992 and Japanese Patent Application Laid-open No. 148340/1993. The various novel polythiol compounds which can be used as the materials of these thiourethanes have also been suggested. That is to say, Japanese Patent Application Laid-open No. 148340/1993 has suggested a branched polythiol compound having 4 sulfur atoms in one molecule; Japanese Patent Application Laid-open No. 270859/1990 has suggested a branched polythiol compound having 5 sulfur atoms in one molecule; and Japanese Patent Application Laid-open No. 192250/1994 has suggested a polythiol compound having a dithian ring structure in one molecule. Additionally, in Japanese Patent Laid-open No. 81320/1991, there has been suggested a process for preparing a lens material by the use of a compound obtained by converting, into an episulfide group, a part or all of the epoxy groups of each of epoxy compounds such as known amine epoxy resins, phenolic epoxy resins, alcoholic epoxy resins, unsaturated compounds-containing epoxy resins, glycidyl ester epoxy resins, urethane epoxy resins and alicyclic epoxy resins. The thiourethane resin lenses which can be obtained by the polythiol compounds and the polyisocyanate compounds can possess a refractive index as high as about 1.66. However, episulfide resin lenses which can be obtained from episulfide compounds derived from known epoxy resins have a refractive index of at most about 1.6. Anyway, the problems of further thinning and reducing the weight of the lenses can be solved to some extent by these conventional sulfur-containing compounds, but needless to say, a further higher refractive index is desirable. On the other hand, another important performance required for the optical material is that the chromatic aberration is low. The higher the Abbe's number is, the lower this chromatic aberration is, and therefore a material having the high Abbe's number is desired. That is to say, the simultaneous achievement of the high refractive index and the high Abbe's number is also desired. However, the Abbe's number usually tends to decline with the increase in the refractive index, and in plastic materials obtained by using conventional diethylene glycol bisallyl carbonate, known episulfide compounds and conventional compounds such as the polythiol compounds and the polyisocyanate compounds as raw materials, the Abbe's number is in the range of about 50 to 55 in the case of a refractive index of 1.5 to 1.55, and it is about 40 in the case of a refractive index of 1.60 and it is at most about 32 in the case of a refractive index of 1.66. On the other hand, the improvement of the heat resistance has often been tried by the use of a polyfunctional compound and a cross-linking agent, but in general, for the expression of the high refractive index, the molecular weight of the material compound is increased, so that a crosslink density decreases. For the expression of the high Abbe's number, an alkyl group content is increased, so that the stiffness of molecules constituting the material compound deteriorates and a sufficient improvement effect has not been obtained yet.

In the conventional optical materials obtained from the episulfide compounds and the combinations of the polythiol compounds and the isocyanate compounds, the increase in the refractive index is limited, and this increase in the refractive index leads to the deterioration of the Abbe's number. Therefore, there has been a problem that the sufficiently high refractive index and Abbe's number cannot be balanced with each other. Furthermore, the improvement of the above-mentioned optical properties, i.e., the refractive index and the Abbe's number leads to the deterioration of the heat resistance, and therefore there has been a problem that while the sufficiently high refractive index and Abbe's number are balanced with each other, the excellent heat resistance cannot be obtained.

SUMMARY OF THE INVENTION

An object of the present invention is to provide a novel sulfur-containing compound which can become an optical material having a small thickness and a low chromatic aberration.

Another object of the present invention is to provide a novel sulfur-containing compound which can become an optical material having a small thickness, a low chromatic aberration and a high heat resistance.

Still another object of the present invention is to provide a novel optical material having such excellent optical properties as mentioned above.

That is to say, the present invention is directed to an alkyl sulfide type episulfide compound represented by the general formula (I) or (II)

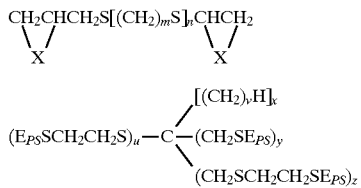 (I)

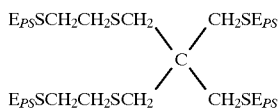 (II)

In the general formula (I), m is an integer of 1 to 6; n is an integer of 0 to 4; X is S or O, and the ratio of S is, on the average, 50% or more of the total of S and O constituting a three-membered ring. Furthermore, in the general formula (II), x is an integer of 0 to 1; y is an integer of 0 to 4; z is an integer of 0 to 4; u is an integer of 0 to 1; v is an integer of 0 to 3; the relation of x+y+z+u=4 is met; and $E_{ps}$ is a

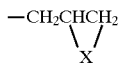

group wherein X is the same as X in the above-mentioned general formula (I).

In this general formula (II), for example, in the case that y is plural, y $CH_2SE_{ps}$ bond to carbon atoms, respectively, and similarly in the case that z is plural, z $CH_2SCH_2CH_2SE_{ps}$ bond to carbon atoms, respectively. That is to say, for example, in the case of u=0, x=0, y=2 and z=2, the general formula (II) is as follows:

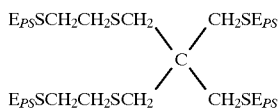

and in the case of u=0, x=0, y=4 and z=0, the general formula (II) is as follows:

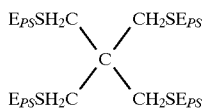

In addition, the present invention is directed to an optical material which is obtainable by polymerizing and curing an alkyl sulfide type episulfide compound represented by the general formula (I) or (II).

DESCRIPTION OF THE PREFERRED EMBODIMENTS

A compound represented by the general formula (I) is a straight-chain alkyl sulfide type episulfide compound. In this general formula (I), n is an integer of 0 to 4, preferably 0 to 3, more preferably 0 to 2, and m is an integer of 1 to 6, preferably 2 to 4, more preferably 2 or 3, most preferably 2. In the same formula (I), X is S or O, but the ratio of S is, on the average, 50% or more, preferably 80 to 100%, more preferably 90 to 100%, much more preferably 95 to 100%, most preferably 100% of the total of S and O constituting a three-membered ring. If n is more than 4, the heat resistance of an optical material obtained by polymerization/curing deteriorates, and such an optical material is unusable. With regard to the heat resistance, it is advantageous that the value of n is as small as 4 or less. If m is too large, a sulfur content is low, so that the high refractive index cannot be achieved, and what is worse, the heat resistance of the material also deteriorates. If m is 1, the compound is thermally slightly unstable, so that in the preparation of the compound according to the present invention, sufficient attention is required for the establishment of conditions and the like. If the ratio of S in X is, on the average, less than 50% of the total of S and O constituting a three-membered ring, the sulfur content is low, so that the high refractive index cannot be achieved. In addition, the reactivity of the compound deteriorates and therefore high-temperature conditions are necessary for the polymerization, so that the optical material obtained by the polymerization/curing is inconveniently colored. The performance of the compound according to the present invention and the performance of the optical material obtained by polymerizing/curing this compound depend upon the integers of n and m as well as the ratio of S in X, as described above. Preferable examples include compounds in which n is 0 or in the range of 1 to 4 and m is in the range of 2 to 4. Above all, more preferable examples include compounds in which n is 0 or in the range of 1 to 3 and m is in the range of 2 to 4. Among these examples, much more preferable embodiments are compounds in which n is 0 or in the range of 1 to 3 and m is in the range of 2 to 4. Above all, particularly preferable compounds (i.e., n is 0, n is 1, and m is in the range of 2 to 4, and n is 2 and m is 2) will be enumerated.

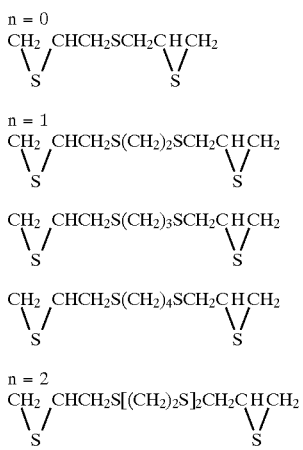

Among these examples, the compounds represented by the following formulae are most preferable.

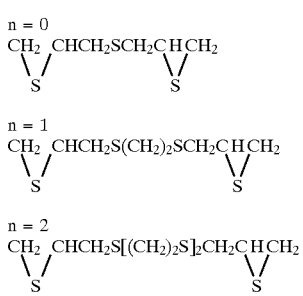

The novel straight-chain alkyl sulfide type episulfide compound of the present invention represented by the general formula (I) can be prepared by various methods, but for example, it can be prepared by reacting a dimercaptan compound having a straight-chain alkyl sulfide structure represented by the general formula (III)

$$HS[(CH_2)_mS]_nH \quad \text{(III)}$$

with an epihalohydrin typified by epichlorohydrin in the presence of an alkali to obtain a straight-chain alkyl sulfide type epoxy compound represented by the general formula (IV)

$$\underset{O}{CH_2\underset{\diagdown\diagup}{\phantom{X}}CHCH_2S[(CH_2)_mS]_nCH_2}\underset{O}{\underset{\diagdown\diagup}{C}H\phantom{X}CH_2} \quad \text{(IV)}$$

and then reacting this epoxy compound with a sulfurizing agent such as a thiocyanate, thiourea, triphenylphosphine sulfide or 3-methylbenzothiazole-2-thione, preferably the thiocyanate or thiourea. In preparing the epoxy compound represented by the above-mentioned general formula (IV), epichlorohydrin is preferable as the epihalohydrin compound. Furthermore, the epihalohydrin compound is stoichiometrically used in an amount of 2 mol per mol of the dimercaptan compound having the general formula (III), but in view of the purity, the reaction rate, the economy and the like of the product, the epihalohydrin compound may be used in a greater amount or in a lesser amount than described above. The epihalohydrin compound is preferably used for the reaction in an amount of 2 to 10 mol, more preferably 2 to 5 mol per mol of the dimercaptan compound. The reaction may be carried out in the absence or presence of a solvent, but when the solvent is used, it is desirable to use the solvent in which any one of the epihalohydrin, the dimercaptan compound of the general formula (III) or a metallic salt of the dimercaptan compound is soluble. Typical examples of such a solvent include water, alcohols, ethers, aromatic hydrocarbons, halogenated hydrocarbons and mixtures thereof. The reaction easily proceeds in the presence of a base. Examples of the base include pyridine, tertiary amines such as triethylamine and diaza-bicycloundecene, and hydroxides of alkali metals and alkaline earth metals. Above all, the hydroxides of the alkali metals and the alkaline earth metals are preferable, and sodium hydroxide and potassium hydroxide are more preferable. A reaction temperature is usually in the range of 0° to 100° C., preferably 30° to 60° C. A reaction time may be a time taken to complete the reaction under the above-mentioned various conditions, but a reaction time of 10 hours or less is usually suitable. In the process for preparing the episulfide compound of the general formula (I) from the epoxy compound represented by the general formula (IV), when the thiocyanate is used as the sulfurizing agent, the thiocyanate is preferably a salt of an alkali metal or an alkaline earth metal, more preferably potassium thiocyanate or sodium thiocyanate. Furthermore, the thiocyanate is stoichiometrically used in an amount of 2 mol per mol of the epoxy compound having the general formula (IV), but in view of the purity, the reaction rate, the economy and the like of the product, the thiocyanate may be used in a greater amount or in a less amount than described above. The thiocyanate is preferably used for the reaction in an amount of 2 to 10 mol, more preferably 2 to 5 mol per mol of the epoxy compound. The reaction may be carried out in the absence or presence of a solvent, but when the solvent is used, it is desirable to use the solvent in which either of the thiocyanate and the epoxy compound of the general formula (IV) is soluble. Typical examples of such a solvent include water, alcohols, ethers, aromatic hydrocarbons, halogenated hydrocarbons and mixtures thereof. A reaction temperature is usually in the range of 0° to 100° C., preferably 20° to 70° C. A reaction time may be a time taken to complete the reaction under the above-mentioned various conditions, but a reaction time of 20 hours or less is usually suitable. As a preparation process other than mentioned above, there is also a process which comprises forming the epoxy compound of the general formula (IV) by oxidizing a corresponding unsaturated compound of the general formula (V)

$$CH_2=CHCH_2S[(CH_2)_mS]_nCH_2CH=CH_2 \quad \text{(V)}$$

with an organic peracid, an alkylhydroxy peroxide, hydrogen peroxide or the like, and then converting this epoxy compound into the episulfide compound of the general formula (I) in the same manner as described above.

The unsaturated compound of the general formula (V) can be prepared by, for example, condensing the dimercaptan compound of the general formula (III) and an allyl halide compound such as allyl chloride or allyl bromide in the presence of a base. Furthermore, another effective process is also present which comprises the dehalogenation-hydrogenation reaction of a dihalodimercaptan compound represented by the general formula (VI)

$$X^1CH_2CHSHCH_2S[(CH_2)_mS]_nCH_2CHSHCH_2X^1 \quad \text{(VI)}$$

wherein $X^1$ is a chlorine atom or a bromine atom.

It is known that the dihalodimercaptan compound represented by the general formula (VI) can easily be synthesized from the unsaturated compound of the general formula (V) and sulfur chloride or the like [e.g., F. Lautenschlaerger et al., J. Org. Chem., Vol. 34, p. 396 (1969)].

On the other hand, the compound represented by the above-mentioned general formula (II) is a branched alkyl sulfide type episulfide compound, but the compound represented by the general formula (II) can be expressed in more detail as follows. In the following expressions, for example, (x=0, y=4, z=0, u=0) represents the structure of the corresponding branched alkyl sulfide type episulfide compound of the general formula (II) in which the respective integers of x, y, z and u are values in parentheses, respectively.

(a) In the case of x=0

(x=0, y=4, z=0, u=0), (x=0, y=3, z=1, u=0), (x=0, y=3, z=0, u=1), (x=0, y=2, z=2, u=0), (x=0, y=2, z=1, (x=0, y=1, z=3, u=0), (x=0, y=1, z=2, u=1), (x=0, y=0, z=u=0), (x=0, y=0, z=3, u=1)

(b) In the case of x=1 and v=0

(x=1, y=3, z=0, u=0), (x=1, y=2, z=1, u=0), (x=1, y=2, z=0, u=1), (x=1, y=1, z=2, u=0), (x=1, y=1, z=1, u=1), (x=1, y=0, z=3, u=0), (x=1, y=1, z=2, u=1), (x=1, y=0, u=1)

(c) In the case of x=1 and v=1

(x=1, y=3, z=0, u=0), (x=1, y=2, z=1, u=0), (x=1, y=2, z=0, u=1), (x=1, y=1, z=2, u=0), (x=1, y=1, z=1, (x=1, y=0, z=3, u=0), (x=1, y=0, z=2, u=1)

(d) In the case of x=1 and v=2

(x=1, y=3, z=0, u=0), (x=1, y=2, z=1, u=0), (x=1, y=2, z=0, u=1), (x=1, y=1, z=2, u=0), (x=1, y=1, z=1, u=1), (x=1, y=0, z=3, u=0), (x=1, y=0, z=4, u=0), (x=1, y=0, z=2, u=1)

(e) In the case of x=1 and v=3

(x=1, y=3, z=0, u=0), (x=1, y=2, z=1, u=0), (x=1, y=2, z=0, u=1), (x=1, y=1, z=2, u=0), (x=1, y=1, z=1, u=1), (x=1, y=0, z=3, u=0), (x=1, y=0, z=2, u=1)

Above all, the cases (a) of x=0 and the cases (b) to (d) of x=1 and v=0 to 2 are preferable, and in the case (a) of x=0 (a), the following compounds of u=0 and y+z=4 are more preferable:

(x=0, y=4, z=0, u=0), (x=0, y=3, z=1, u=0), (x=0, y=2, z=2, u=0), (x=0, y=1, z=3, u=0), (x=0, y=0, z=4, u=0).

In the case (b) of x=1 and v=0, the following compounds of u=1 and y+z=2 are preferable:

(x=1, y=2, z=0, u=1), (x=1, y=1, z=1, u=1), (x=1, y=0, z=2, u=1).

In the cases (c) and (d) of x=1 and v=1 to 2, the following compounds of u=0 and y+z=3 are preferable:

(x=1, y=3, z=0, u=0), (x=1, y=2, z=1, u=0), (x=1, y=1, z=2, u=0), and (x=1, y=0, z=3, u=0).

Most preferable are (x=0, y=4, z=0, u=0) in the case (a) of x=0; (x=1, y=2, z=0, u=1) and (x=1, y=1, z=1, u=1) in the case (b) of x=1 and v=0; and (x=1, y=3, z=0, u=0) in the cases (c) and (d) of x=1 and v=1 to 2.

The most preferable examples of the compound represented by the general formula (II) will be enumerated by structural formulae in the above-mentioned order as follows.

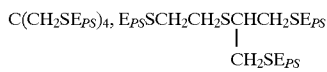

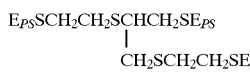

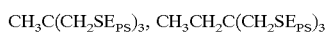

In the above-mentioned general formula (II), X is S or O, as in the above-mentioned general formula (I), but the ratio of S is, on the average, 50% or more, preferably 80 to 100%, more preferably 90 to 100%, much more preferably 95 to 100%, most preferably 100% of the total of S and O constituting the three-membered ring. The preferable examples, the more preferable examples and the most preferable examples of the novel branched alkyl sulfide type episulfide compound represented by the general formula (II) of the present invention have hereinbefore been shown, but the grounds of such a ranking are as follows. If the molecular weight of a branch portion constituting a branch of the episulfide compound is too large, the heat resistance of the optical material which can be obtained by polymerizing/curing the compound cannot sufficiently be exerted, and if a sulfur content is low, the sufficiently high refractive index cannot be obtained (this tendency is particularly noticeable, when the compound is polymerized/cured together with another compound). Furthermore, if the ratio of S in X is, on the average, less than 50% of the total of S and O constituting the three-membered ring, the sulfur content is low, so that the high refractive index cannot be achieved. In addition, the reactivity of the compound deteriorates, so that high-temperature conditions are necessary for the polymerization, with the result that the optical material is inconveniently colored. Moreover, another ground is that if a similar effect is obtained, the structure not having many branches is preferable for the sake of avoiding the complexity of the preparation process.

The novel branched alkyl sulfide type episulfide compound represented by the general formula (II) of the present invention can be prepared by various methods, but for example, a trimercaptan compound or a tetramercaptan compound having a branched alkyl sulfide structure represented by the following general formula (VII) is reacted with an epihalohydrin typified by epichlorohydrin in the presence of an alkali to obtain a branched alkyl sulfide type epoxy compound represented by the following general formula (VIII):

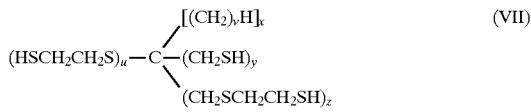

wherein x is an integer of 0 or 1; y is an integer of 0 to 4; z is an integer of 0 to 4; u is an integer of 0 or 1; and v is an integer of 0 to 3; and the relation of x+y+z+u=4 is met, and

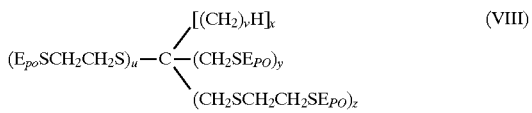

wherein x is an integer of 0 or 1; y is an integer of 0 to 4; z is an integer of 0 to 4; u is an integer of 0 or 1; and v is an integer of 0 to 3; the relation of x+y+z+u=4 is met; and $E_{po}$ is a

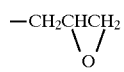

group.

Next, the thus obtained epoxy compound is reacted with a sulfurizing agent such as a thiocyanate, thiourea, triphenylphosphine sulfide or 3-methylbenzothiazole-2-thione, preferably the thiocyanate or thiourea. In preparing the epoxy compound represented by the general formula (VIII), epichlorohydrin is preferable as the epihalohydrin compound. Furthermore, the epihalohydrin compound is stoichiometrically used in an amount of 3 to 4 mol per mol of the trimercaptan compound or the tetramercaptan compound having the general formula (VII), but in view of the purity, the reaction rate, the economy and the like of the product, the epihalohydrin compound may be used in a greater amount or in a less amount than described above. The epihalohydrin compound is preferably used for the reaction in an amount of 1 to 5 mol, more preferably 1 to 2.5 mol per mol of the trimercaptan compound or the tetramercaptan compound. The reaction may be carried out in the absence or presence of a solvent, but when the solvent is used, it is desirable to use the solvent in which any one of the epihalohydrin, the dimercaptan compound of the general formula (VII) or a metallic salt of the dimercaptan compound is soluble. Typical examples of such a solvent include water, alcohols, ethers, aromatic hydrocarbons and halogenated hydrocarbons. The reaction easily proceeds in the presence of a base. Examples of the base include pyridine, tertiary amines such as triethylamine and diazabicycloundecene, and hydroxides of alkali metals and alkaline earth metals. Above all, the hydroxides of the alkali metals and the alkaline earth metals are preferable, and sodium hydroxide and potassium hydroxide are more preferable. A reaction temperature is usually in the range of 0° to 100° C., preferably 30° to 60° C. A reaction time may be a time taken to complete the reaction under the above-mentioned various conditions, but a reaction time of 10 hours or less is usually suitable. In the process for preparing the episulfide compound of the general formula (II) from the epoxy compound represented by the general formula (VIII), when the thiocyanate is used as the sulfurizing agent, the thiocyanate is preferably a salt of an alkali metal or an alkaline earth metal, more preferably potassium thiocyanate or sodium thiocyanate. Furthermore, the thiocyanate is stoichiometrically used in an amount of 3 to 4 mol per mol of the epoxy compound having the general formula (VIII), but in view of the purity, the reaction rate, the economy and the like of the product, the thiocyanate may be used in a more amount or in a less amount than described above. The thiocyanate is preferably used for the reaction in an amount of 1 to 5 mol, more preferably 1 to 2.5 mol per mol of the epoxy compound. The reaction may be carried out in the absence or presence of a solvent, but when the solvent is used, it is desirable to use the solvent in which either of the thiocyanate and the epoxy compound of the general formula (VIII) is soluble. Typical examples of such a solvent include water, alcohols, ethers, aromatic hydrocarbons and halogenated hydrocarbons. A reaction temperature is usually in the range of 0° to 100° C., preferably 20° to 70° C. A reaction time may be a time taken to complete the reaction under the above-mentioned various conditions, but a reaction time of 20 hours or less is usually suitable. As a preparation process other than mentioned above, there is also a process which comprises forming the epoxy compound of the general formula (VIII) by oxidizing a corresponding unsaturated compound of the general formula (IX) with an organic peracid, an alkylhydroxy peroxide, hydrogen peroxide or the like, and then converting this epoxy compound into the episulfide compound of the general formula (II) in the same manner as described above:

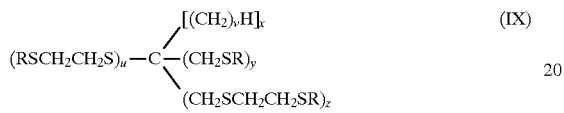

(IX)

wherein x is an integer of 0 or 1; y is an integer of 0 to 4; z is an integer of 0 to 4; u is an integer of 0 or 1; and v is an integer of 0 to 3; the relation of x+y+z+u=4 is met; and R is a $CH_2=CHCH_2-$ group.

The unsaturated compound of the general formula (IX) can be prepared by, for example, condensing the branched dimercaptan compound of the general formula (VII) and an allyl halide compound such as allyl chloride or allyl bromide in the presence of a base. Furthermore, another effective process is also present which comprises the dehalogenation-hydrogenation reaction of a trihalotrimercaptan compound represented by the following general formula (X) or a tetrahalotetramercaptan compound:

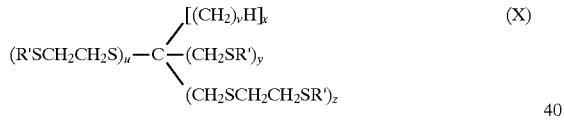

(X)

wherein x is an integer of 0 or 1; y is an integer of 0 to 4; z is an integer of 0 to 4; u is an integer of 0 or 1; and v is an integer of 0 to 3; the relation of x+y+z+u=4 is met; R' is a $X^1CH_2CHSHCH_2-$ group, and $X^1$ is a chlorine atom or a bromine atom.

It is known that the halomercaptan compound of the general formula (X) can easily be synthesized from the unsaturated compound of the general formula (IX) and sulfur chloride or the like [e.g., F. Lautenschlaerger et al., J. Org. Chem., Vol. 34, p. 396 (1969)].

One or more of the novel alkyl sulfide type episulfide compounds of the present invention [the straight-chain type of the general formula (I) and the branched type of the general formula (II)] can be polymerized/cured in the presence of a curing catalyst to prepare an optical material. In this polymerization, any of the known curing catalysts for epoxy resins can be used. Typical examples of the curing catalysts include (1) amine compounds typified by primary amines such as ethylamine, n-propylamine, sec-propylamine, n-butylamine, sec-butylamine, iso-butylamine, tertbutylamine, pentylamine, hexylamine, heptylamine, octylamine, decylamine, laurylamine, myristylamine, 1,2-dimethylhexylamine, 3-pentylamine, 2-ethylhexylamine, allylamine, aminoethanol, 1-aminopropanol, 2-aminopropanol, aminobutanol, aminopentanol, aminohexanol, 3-ethoxypropylamine, 3-propoxypropylamine, 3-isopropoxypropylamine, 3-butoxypropylamine, 3-isobutoxypropylamine, 3-(2-ethylhexyloxy)propylamine, aminocyclopentane, aminocyclohexane, aminonorbornene, aminomethylcyclohexane, amonobenzene, benzylamine, phenethylamine, α-phenylethylamine, naphthylamine and furfurylamine; primary polyamines such as ethylenediamine, 1,2-diaminopropane, 1,3-diaminopropane, 1,2-diaminobutane, 1,3-diaminobutane, 1,4-diaminobutane, 1,5-diaminopentane, 1,6-diaminohexane, 1,7-diaminoheptane, 1,8-diaminooctane, dimethylaminopropylamine, diethylaminopropylamine, bis-(3-aminopropyl)ether, 1,2-bis-(3-aminopropoxy)ethane, 1,3-bis-(3-aminopropoxy)-2,2'-dimethylpropane, amonoethylethanolamine, 1,2-bisaminocyclohexane, 1,3-bisaminocyclohexane, 1,4-bisaminocyclohexane, 1,3-bisaminomethylcyclohexane, 1,4-bisaminomethylcyclohexane, 1,3-bisaminoethylcyclohexane, 1,4-bisaminoethylcyclohexane, 1,3-bisaminopropylcyclohexane, 1,4-bisaminopropylcyclohexane, hydrogenated 4,4'-diamonodiphenylmethane, 2-aminopiperidine, 4-aminopiperidine, 2-aminomethylpiperidine, 4-aminomethylpiperidine, 2-aminoethylpiperidine, 4-aminoethylpiperidine, N-aminoethylpiperidine, N-aminopropylpiperidine, N-aminoethylmorpholine, N-aminopropylmorpholine, isophoronediamine, methanediamine, 1,4-bisaminopropylpiperazine, o-phenylenediamine, m-phenylenediamine, p-phenylenediamine, 2,4-tolylenediamine, 2,6-tolylenediamine, 2,4-toluenediamine, m-aminobenzylamine, 4-chloro-o-phenylenediamine, tetrachloro-p-xylylenediamine, 4-methoxy-6-methyl-m-phenylenediamine, m-xylylenediamine, p-xylylenediamine, 1,5-naphthalenediamine, 2,6-naphthalenediamine, benzidine, 4,4'-bis(o-toluidine), dianisidine, 4,4'-diaminodiphenylmethane, 2,2-(4,4'-diaminodiphenyl)propane, 4,4'-diamino diphenyl ether, 4,4'-thiodianiline, 4,4'-diaminodiphenylsulfone, 4,4'-diaminoditolylsulfone, methylenebis(o-chloroaniline), 3,9-bis(3-aminopropyl)-2,4,8,10-tetraoxaspiro[5.5] undecane, diethylenetriamine, iminobispropylamine, methyliminobispropylamine, bis(hexamethylene) triamine, triethylenetetramine, tetraethylenepentamine, pentaethylenehexamine, N-aminoethylpiperazine, N-aminopropylpiperazine, 1,4-bis (aminoethylpiperazine), 1,4-bis (aminopropylpiperazine), 2,6-diaminopyridine and bis (3,4-diaminophenyl)sulfone; secondary amines such as diethylamine, dipropylamine, di-n-butylamine, di-secbutylamine, diisobutylamine, di-n-pentylamine, di-3-pentylamine, dihexylamine, octylamine, di(2-ethylhexyl)amine, methylhexylamine, diallylamine, pyrrolidine, piperidine, 2-picoline, 3-picoline, 4-picoline, 2,4-lupetidine, 2,6-lupetidine, 3,5-lupetidine, diphenylamine, N-methylaniline, N-ethylaniline, dibenzylamine, methylbenzylamine, dinaphthylamine, pyrrole, indoline, indole and morpholine; secondary polyamines such as N,N'-dimethylethylenediamine, N,N'-dimethyl-1,2-diaminopropane, N,N'-dimethyl-1,3-diaminopropane, N,N'-dimethyl-1,2-diaminobutane, N,N'-dimethyl-1,3-diaminobutane, N,N'-dimethyl-1,4-diaminobutane, N,N'-dimethyl-1,5-diaminopentane, N,N'-dimethyl-1,6-diaminohexane, N,N'-dimethyl-1,7-diaminoheptane, N,N'-diethylethylenediamine, N,N'-diethyl-1,2-diaminopropane, N,N'-diethyl-1,3-diaminopropane, N,N'-diethyl-1,2-diaminobutane, N,N'-diethyl-1,3-diaminobutane, N,N'-diethyl-1,4-diaminobutane, N,N'-diethyl-1,6-diaminohexane, piperazine, 2-methylpiperazine, 2,5-dimethylpiperazine, 2,6-dimethylpiperazine, homopiperazine, 1,1-di-(4-piperidyl)methane, 1,2-di-(4-piperidyl)ethane, 1,3-di-(4-piperidyl)propane, 1,4-di-(4-piperidyl)butane and tetramethylguanidine; tertiary amines such as trimethylamine, triethylamine, tri-n-propylamine, tri-iso-propylamine, tri-1,2-dimethylpropylamine, tri-3-methoxypropylamine, tri-n-butylamine, tri-isobutylamine, tri-sec-butylamine, tripentylamine, tri-3-pentylamine, tri-n-hexylamine, tri-n-octylamine, tri-2-ethylhexylamine, tri-dodecylamine, tri-laurylamine, tricyclohexylamine, N,N-dimethylhexylamine, N-methyldihexylamine, N,N-dimethylcyclohexylamine, N-methyldicyclohexylamine, triethanolamine, tribenzylamine, N,N-dimethylbenzylamine, diethylbenzylamine, triphenylamine, N,N-dimethylamino-p-cresol, N,N-dimethylaminomethylphenol, 2-(N,N-dimethylaminomethyl)phenol, N,N-dimethylaniline, N,N-diethylaniline, pyridine, quinoline, N-methylmorpholine, N-methylpiperidine and 2-(2-dimethylaminoethoxy)-4-methyl-1,3,2-dioxabornane; tertiary polyamines such as tetramethylethylenediamine, pyrazine, N,N'-dimethylpiperazine, N,N'-bis((2-hydroxy)propyl)piperazine, hexamethylenetetramine, N,N,N',N'-tetramethyl-1,3-butaneamine, 2-dimethylamino-2-hydroxypropane, diethylaminoethanol, N,N,N-tris(3-dimethylaminopropyl)amine, 2,4,6-tris(N,N-dimethylaminomethyl)phenol and heptamethylisobiguanide; various imidazoles such as imidazole, N-methylimidazole, 2-methylimidazole, 4-methylimidazole, N-ethylimidazole, 2-ethylimidazole, 4-ethylimidazole, N-butylimidazole, 2-butylimidazole, N-undecylimidazole, 2-undecylimidazole, N-phenylimidazole, 2-phenylimidazole, N-benzylimidazole, 2-benzylimidazole, 1-benzyl-2-methylimidazole, N-(2'-cyanoethyl)-2-methylimidazole, N-(2'-cyanoethyl)-2-undecylimidazole, N-(2'-cyanoethyl)-2-phenylimidazole, 3,3-bis-(2-ethyl-4-methylimidazolyl)methane, adducts of alkylimidazoles with isocyanuric acid, and condensates of alkylimidazoles and formaldehyde; amidines such as 1,8-diazabicyclo[5.4.0]-undecene-7, 1,5-diazabicyclo[4.3.0]nonene-5 and 6-dibutylamino-1,8-diazabicyclo[5.4.0]undecene-7, (2) quaternary ammonium salts of the amine in the above-mentioned paragraph (1) and halogens, mineral acids, Lewis acids, organic acids, silicic acid, boron tetrafluoride and the like, (3) complexes of the amines in the above-mentioned paragraph (1), borane and boron trifluoride, and (4) phosphines such as trimethylphosphine, triethylphosphine, tri-iso-propylphosphine, tri-n-butylphosphine, tricyclohexylphosphine, triphenylphosphine, tribenzylphosphine, dimethylphenylphosphine, diethylphenylphosphine, ethyldiphenylphosphine, chlorodiphenylphosphine, tri-n-hexylphosphine, tri-n-octylphosphine, diphenylcyclohexylphosphine, dicyclohexylphenylphosphine, tris(2-methylphenyl) phosphine, tris(3-methylphenyl)phosphine, tris(4-methylphenyl)phosphine and tris(diethylamino) phosphine.

They may be used singly or in a combination of two or more thereof.

The novel alkyl sulfide type episulfide compound of the present invention can be cured/polymerized with a compound having two or more functional groups which can react with an episulfide group, or a compound having one or more of these functional groups and one or more of other homopolymerizable functional groups, thereby preparing an optical material. Examples of the compound having two or more functional groups include epoxy compounds, sulfur-containing epoxy compounds, known episulfide compounds, polyvalent carboxylic acids, polyvalent carboxylic anhydrides, mercaptocarboxylic acids, polymercaptans, mercaptoalcohols, mercaptophenols, polyphenols, amines and amides. Examples of the compound having one or more of these functional groups and one or more of other homopolymerizable functional groups include episulfide compounds of epoxy compounds having unsaturated groups such as vinyl, aromatic vinyl, methacryl, acryl and allyl as well as sulfur-containing epoxy compounds, carboxylic acids, carboxylic anhydrides, mercaptocarboxylic acids, mercaptans, phenols, amines and amides.

In polymerizing/curing the novel alkyl sulfide type episulfide compound of the present invention to obtain the optical material, it is, needless to say, possible that additives such as a known antioxidant and ultraviolet light absorber can be added to further improve the practicality of the obtained material. Furthermore, a known external release agent and/or internal release agent can be used or added for the purpose of improving the mold release characteristics of the cured material from a mold. Examples of the internal release agent referred to herein include fluorine-containing nonionic surface active agents, silicon-containing nonionic surface active agents, alkyl quaternary ammonium salts, phosphoric acid esters, acidic phosphoric acid esters, alkali metal salts of the acidic phosphoric acid esters, metal salts of higher fatty acids, higher fatty acid esters, paraffins, waxes, higher aliphatic amides, higher aliphatic alcohols, polysiloxanes and adducts of aliphatic amines with ethylene oxides.

In the case that the novel alkyl sulfide type episulfide compound of the present invention as a starting material is polymerized/cured, if necessary, by the use of the above-mentioned curing catalyst and a compound such as glycidyl methacrylate which can react with an episulfide group having an unsaturated group in order to obtain an optical material, these materials are mixed with additives such as a radical polymerization initiator, a radically polymerizable monomer, a release agent, an antioxidant and an ultraviolet light absorber, and the mixture is then polymerized/cured by the following procedure to obtain an optical material such as a lens. That is to say, the mixed material is poured into a glass mold or a metal mold, and a polymerizing/curing reaction is then allowed to proceed by heating. Afterward, the thus cured material is released from the mold. A curing time is in the range of 0.1 to 100 hours, usually 1 to 48 hours, and a curing temperature is in the range of −10° to 160° C., usually −10° to 140° C. Alternatively, after the completion of the curing, the material may be subjected to an annealing treatment at a temperature of 50° to 150° C. for a period of 10 minutes to 5 hours, and this annealing treatment is preferable to remove strain from the optical material of the present invention. Furthermore, if necessary, a surface treatment suitable for the formation of a hard coat, the prevention of reflection, the impartment of fog resistance or the like can selectively be carried out.

Next, the present invention will be described in detail with reference to examples, but the scope of the present invention should not be limited to these examples. Incidentally, the physical properties of obtained polymers were measured by the following procedures.

Refractive index ($N_D$) and Abbe's number ($v_D$): They were measured at 25° C. by the use of an Abbe's refractometer.

Specific gravity: It was measured at 25° C. by the use of an electron gravimeter, and then calibrated in a usual manner.

Heat resistance: A product having a Vicat softening point of 120° C. or more was represented by ○, a product having a softening point of less than 120° C. and 80° C. or more was represented by Δ, and a product having a softening point of less than 80° C. was represented by X.

Strength: In accordance with a three-point bending test using an autograph, a product having a bend of 10 mm or more was represented by ○, a product having a bend of less than 10 mm and 5 mm or more was represented by Δ, and a product having a bend of less than 5 mm was represented by X.

EXAMPLE 1
(in the general formula (I), n=1 and m=2)

In a flask equipped with a stirrer, a dropping funnel, a thermometer and a nitrogen introducing tube were placed 94.2 g (1.0 mol) of 1,2-dimercaptoethane, an aqueous solution obtained by dissolving 0.4 g (10 mmol) of sodium hydroxide in 4 ml of water and 100 ml of methanol, and 2.0 mol (185.0 g) of epichlorohydrin was then added dropwise over 1 hour. During the dropping, a reaction temperature was maintained at 0° to 10° C. After the completion of the dropping, the reaction was further continued for 1 hour. Afterward, 240 g (6.0 mol) of caustic soda dissolved in 360 ml of water was added dropwise over 1 hour. During the dropping, a reaction temperature was maintained at 0° to 10° C. After the completion of the dropping, the reaction was further continued for 3 hours. After extraction with toluene and washing with water, the used solvent was distilled off to obtain 202.0 g (99% of a theoretical amount) of 1,2-bis (glycidylthio)ethane in the state of a colorless transparent liquid.

Next, in a flask equipped with a stirrer, a thermometer and a nitrogen introducing tube were placed 79.9 g (0.3 mol) of the thus obtained 1,2-bis(glycidylthio)ethane, 95.3 g (1.25 mol) of thiourea, 2.96 g (0.03 mol) of acetic anhydride and 250 ml of toluene as well as 250 ml of methanol as solvents, and reaction was then carried out at 30° C. for 9 hours. After the reaction, the reaction solution was extracted with toluene, and the resulting extract was washed with a 1% aqueous sulfuric acid solution and then water. Afterward, the excessive solvents were distilled off to obtain 82.0 g (93% of a theoretical amount) of 1,2-bis(β-epithiopropylthio) ethane (in the general formula (I), m=2 and n=1) in the state of a white solid.

| Elemental analysis: | | Found | Calcd. |
|---|---|---|---|
| | C | 40.19% | 40.30% |
| | H | 6.05% | 5.95% |
| | S | 53.79% | 53.64% |

Mass spectrum (EI): M$^+$ 238 (theoretical molecular weight=238)

Infrared absorption spectrum: 620 cm$^{-1}$ (stretching vibration of an episulfide ring)

$^1$H-NMR:
2.2 ppm (hydrogen atoms bonded to carbon atoms at 1- and 10-positions)
2.6 ppm (hydrogen atoms bonded to carbon atoms at 1- and 10-positions)
2.7 ppm (hydrogen atoms bonded to carbon atoms at 2- and 9-positions)
2.9 ppm (hydrogen atoms bonded to carbon atoms at 5- and 6-positions)
3.0 ppm (hydrogen atoms bonded to carbon atoms at 3- and 8-positions)
3.1 ppm (hydrogen atoms bonded to carbon atoms at 3- and 8-positions)

$^{13}$C-NMR:
25.7 ppm (carbon atoms at 1- and 10-positions)
32.5 ppm (carbon atoms at 2- and 9-positions)
34.0 ppm (carbon atoms at 5- and 6-positions)
38.4 ppm (carbon atoms at 3- and 8-positions)

Furthermore, 1 part by weight of tributylamine was blended with the compound obtained above, and the blend was then poured into a mold comprising 2 glass plates having an adjusted thickness of 2 mm. Afterward, the blend was polymerized/cured at 80° C. for 5 hours to obtain an optical material. The refractive index, the Abbe's number and the specific gravity of the obtained optical material were measured, and the results are shown in Table 1.

EXAMPLE 2
(in the general formula (I), n=1 and m=4)

The same procedure as in Example 1 was repeated except that 1,2-dimercaptoethane was replaced with 1,4-dimercaptobutane, thereby obtaining 1,4-bis(β-epithiopropylthio)butane (in the general formula (I), m=4 and n=1) in a total yield of 85%.

| Elemental analysis: | | Found | Calcd. |
|---|---|---|---|
| | C | 44.89% | 45.07% |
| | H | 6.99% | 6.81% |
| | S | 48.00% | 48.13% |

Mass spectrum (EI): M$^+$ 266 (theoretical molecular weight=266)

Infrared absorption spectrum: 620 cm$^{-1}$ (stretching vibration of an episulfide ring)

$^1$H-NMR:
1.9 ppm (hydrogen atoms bonded to carbon atoms at 6- and 7-positions)
2.2 ppm (hydrogen atoms bonded to carbon atoms at 1- and 12-positions)
2.6 ppm (hydrogen atoms bonded to carbon atoms at 1- and 12-positions)
2.7 ppm (hydrogen atoms bonded to carbon atoms at 2- and 11-positions)
2.8 ppm (hydrogen atoms bonded to carbon atoms at 5- and 8-positions)
3.0 ppm (hydrogen atoms bonded to carbon atoms at 3- and 10-positions)
3.1 ppm (hydrogen atoms bonded to carbon atoms at 3- and 10-positions)

$^{13}$C-NMR:
25.7 ppm (carbon atoms at 1- and 12-positions)
30.5 ppm (carbon atoms at 6- and 7-positions)
31.3 ppm (carbon atoms at 5- and 8-positions)
32.5 ppm (carbon atoms at 2- and 11-positions)
39.1 ppm (carbon atoms at 3- and 10-positions)

After polymerization/curing, the refractive index, the Abbe's number and the specific gravity of an obtained optical material were measured, and the results are shown in Table 1.

EXAMPLE 3
(in the general formula (I), n=2 and m=2)

The same procedure as in Example 1 was repeated except that 1,2-dimercaptoethane was replaced with dimercaptodiethyl sulfide, thereby obtaining bis(β-epithiopropylthioethyl) sulfide (in the general formula (I), m=2 and n=2) in a total yield of 88%.

| Elemental analysis: | | Found | Calcd. |
|---|---|---|---|
| | C | 40.08% | 40.23% |
| | H | 6.22% | 6.08% |
| | S | 53.55% | 53.70% |

Mass spectrum (EI): $M^+$ 298 (theoretical molecular weight=298)

Infrared absorption spectrum: 620 $cm^{-1}$ (stretching vibration of an episulfide ring)

$^1$H-NMR:

2.2 ppm (hydrogen atoms bonded to carbon atoms at 1- and 13-positions)

2.6 ppm (hydrogen atoms bonded to carbon atoms at 1- and 13-positions)

2.7 ppm (hydrogen atoms bonded to carbon atoms at 2- and 12-positions)

2.8–2.9 ppm (hydrogen atoms bonded to carbon atoms at 5-, 6-, 8- and 9-positions)

3.0 ppm (hydrogen atoms bonded to carbon atoms at 3- and 11-positions)

3.1 ppm (hydrogen atoms bonded to carbon atoms at 3- and 11-positions)

$^{13}$C-NMR:

25.7 ppm (carbon atoms at 1- and 13-positions)

32.4 ppm (carbon atoms at 2- and 12-positions)

32.5 ppm (carbon atoms at 6- and 8-positions)

34.0 ppm (carbon atoms at 5- and 9-positions)

38.4 ppm (carbon atoms at 3- and 11-positions)

After polymerization/curing, the refractive index, the Abbe's number and the specific gravity of an obtained optical material were measured, and the results are shown in Table 1.

EXAMPLE 4
(in the general formula (I), n=0)

1.0 mol (34.1 g) of hydrogen sulfide and 1.0 mol (92.5 g) of epichlorohydrin were placed in a completely sealed reaction device, and the solution was cooled to 10° C. Next, an aqueous solution obtained by dissolving 5 mmol (0.2 g) of an aqueous sodium hydroxide solution in 4 ml of water was added to the cooled solution, followed by stirring at this temperature for 1 hour. Afterward, the solution was stirred for 2 hours, while the solution temperature was maintained at about 40° to 45° C. The solution was cooled to 10° C. again, and an aqueous solution obtained by dissolving 1.0 mol (92.5 g) of epichlorohydrin and 5 mmol (0.2 g) of sodium hydroxide in 4 ml of water was further added to the cooled solution, followed by stirring at 10° C. for 1 hour and at 40 to 45° C. for 2 hours. After the solution temperature had been returned to room temperature, an aqueous solution obtained by dissolving 80.0 g (2 mol) of sodium hydroxide in 80 ml of water was added dropwise thereto, while the solution temperature was maintained at about 40° to 45° C., followed by stirring for 3 hours, while the solution temperature was maintained at about 40° to 45° C. After the completion of the reaction, the same treatment as in Example 1 was made to obtain 92.2 g (theoretical amount= 63%) of a product. Next, this product was reacted with thiourea to obtain bis(P-epithiopropyl)sulfide (in the general formula (I), n=0) in a yield of 80%.

| Elemental analysis: | | Found | Calcd. |
|---|---|---|---|
| | C | 40.25% | 40.41% |
| | H | 5.81% | 5.65% |
| | S | 53.77% | 53.94% |

Mass spectrum (EI): $M^+$ 178 (theoretical molecular weight=178)

Infrared absorption spectrum: 620 $cm^{-1}$ (stretching vibration of an episulfide ring)

$^1$H-NMR:

2.3 ppm (hydrogen atoms bonded to carbon atoms at 1- and 7-positions)

2.6 ppm (hydrogen atoms bonded to carbon atoms at 1- and 7-positions)

2.7 ppm (hydrogen atoms bonded to carbon atoms at 2- and 6-positions)

3.0–3.1 ppm (hydrogen atoms bonded to carbon atoms at 3- and 5-positions)

$^{13}$C-NMR:

25.6 ppm (carbon atoms at 1- and 7-positions)

33.8 ppm (carbon atoms at 2- and 6-positions)

38.6 ppm (carbon atoms at 3- and 5-positions)

After polymerization/curing, the refractive index, the Abbe's number and the specific gravity of an obtained optical material were measured, and the results are shown in Table 1.

EXAMPLE 5

The same procedure as in Example 1 was repeated except that 1,2-dimercaptoethane was replaced with 1,6-dimercaptohexane, thereby obtaining 1,6-bis(β-epithiopropylthio)hexane in a total yield of 72%.

| Elemental analysis: | | Found | Calcd. |
|---|---|---|---|
| | C | 48.72% | 48.93% |
| | H | 7.77% | 7.53% |
| | S | 43.30% | 43.54% |

Mass spectrum (EI): $M^+$ 294 (theoretical molecular weight=294)

Infrared absorption spectrum: 620 $cm^{-1}$ (stretching vibration of an episulfide ring)

$^1$H-NMR:

1.6 ppm (hydrogen atoms bonded to carbon atoms at 7- and 8-positions)

1.8 ppm (hydrogen atoms bonded to carbon atoms at 6- and 9-positions)

2.2 ppm (hydrogen atoms bonded to carbon atoms at 1- and 14-positions)

2.6 ppm (hydrogen atoms bonded to carbon atoms at 1- and 14-positions)

2.7 ppm (hydrogen atoms bonded to carbon atoms at 2- and 13-positions)

2.8 ppm (hydrogen atoms bonded to carbon atoms at 5- and 10-positions)

3.0 ppm (hydrogen atoms bonded to carbon atoms at 3- and 12-positions)

3.1 ppm (hydrogen atoms bonded to carbon atoms at 3- and 12-positions)

$^{13}$C-NMR:

25.7 ppm (carbon atoms at 1- and 14-positions)

27.8 ppm (carbon atoms at 7- and 8-positions)
31.6 ppm (carbon atoms at 6- and 9-positions)
32.0 ppm (carbon atoms at 5- and 10-positions)
32.4 ppm (carbon atoms at 2- and 13-positions)
39.0 ppm (carbon atoms at 3- and 12-positions)

After polymerization/curing, the refractive index, the Abbe's number and the specific gravity of an obtained optical material were measured, and the results are shown in Table 1.

Comparative Example 1

The same procedure as in Example 1 was repeated except that 1,2-dimercaptoethane was replaced with 1,2-dihydroxyethane(ethylene glycol), thereby obtaining 1,2-bis(β-epithiopropyloxy)ethane in a total yield of 58%. After polymerization/curing, the refractive index, the Abbe's number and the specific gravity of an obtained optical material were measured, and the results are shown in Table 1.

Comparative Example 2

The same procedure as in Example 2 was repeated except that 1,4-dimercaptobutane was replaced with 1,4-dihydroxybutane(1,4-butanediol), thereby obtaining 1,4-bis(β-epithiopropyloxy)butane in a total yield of 66%. After polymerization/curing, the refractive index, the Abbe's number and the specific gravity of an obtained optical material were measured, and the results are shown in Table 1.

Comparative Example 3

The same procedure as in Example 3 was repeated except that dimercaptodiethyl sulfide was replaced with dihydroxy diethyl ether(diethylene glycol), thereby obtaining bis(β-epithiopropyloxyethyl) ether in a total yield of 68%. After polymerization/curing, the refractive index, the Abbe's number and the specific gravity of an obtained optical material were measured, and the results are shown in Table 1.

Comparative Example 4

The same procedure as in Example 1 was repeated except that thiourea was used in an amount of 0.8 mol per mol of 1,2-bis(glycidylthio)ethane. According to an NMR spectrum, an obtained product had a general formula (I) of n=1 and m=2, and the ratio of S in X was 30% of the total of S and O constituting a three-membered ring on the average. After polymerization/curing, the refractive index, the Abbe's number and the specific gravity of an obtained optical material were measured, and the results are shown in Table 1.

TABLE 1

| | Episulfide Compound | $N_D$ | $v_D$ | Specific Gravity | Heat Resistance | Strength |
|---|---|---|---|---|---|---|
| Example 1 | 1,2-bis(β-epithiopropylthio)ethane | 1.70 | 36 | 1.38 | ○ | ○ |
| Example 2 | 1,4-bis(β-epithiopropylthio)butane | 1.68 | 37 | 1.32 | ○ | ○ |
| Example 3 | Bis(β-epithiopropylthioethyl) sulfide | 1.70 | 36 | 1.35 | ○ | ○ |
| Example 4 | Bis(β-epithiopropyl) sulfide | 1.71 | 35 | 1.40 | ○ | Δ |
| Example 5 | 1,6-bis(β-epithiopropylthio) hexane | 1.67 | 38 | 1.30 | Δ | ○ |
| Comp. Ex. 1 | 1,2-bis(β-epithiopropyloxy)ethane | 1.60 | 42 | 1.30 | Δ | Δ |
| Comp. Ex. 2 | 1,4-bis(β-epithiopropyloxy)butane | 1.59 | 43 | 1.26 | Δ | |
| Comp. Ex. 3 | Bis(β-epithiopropyloxyethyl) ether | 1.58 | 43 | 1.27 | X | ○ |
| Comp. Ex. 4 | In general formula (I) of n = 0 and m = 2, ratio of S in X was 30% of total of S and O on the average. | 1.63 | 41 | 1.33 | X | ○ |

EXAMPLE 6

[in the general formula (II), v=0 (x=1, y=2, z=0 and u=1)]

The same procedure as in Example 1 was repeated except that 1,2-dimercaptoethane was replaced with 2-(2-mercaptoethylthio)-1,3-dimercaptopropane, to obtain 106.6 g (85% of a theoretical amount) of 2-(2-β-epithiopropylthioethylthio)-1,3-bis(β-epithiopropylthio)propane.

| Elemental analysis: | | Found | Calcd. |
|---|---|---|---|
| | C | 45.15% | 40.34% |
| | H | 5.99% | 5.80% |
| | S | 53.69% | 53.85% |

Mass spectrum (EI): $M^+$ 416 (theoretical molecular weight=416)

Infrared absorption spectrum: 620 $cm^{-1}$ (stretching vibration of an episulfide ring)

$^1$H-NMR:
2.2 ppm (hydrogen atoms bonded to carbon atoms at 1-, 13-, and 13'-positions)
2.6–3.1 ppm (hydrogen atoms bonded to carbon atoms at other positions)

$^{13}$C-NMR:
25.7 ppm (carbon atoms at 1-, 13- and 13'-positions)
32.4 ppm (carbon atoms at 2-, 12- and 12'-positions)
32.5 ppm (a carbon atom at 8-position)
34.4 ppm (a carbon atom at 9-position)
37.3 ppm (a carbon atom at 5-position)
38.4 ppm (carbon atoms at 3-, 11- and 11'-positions)
46.0 ppm (a carbon atom at 6-position)

Furthermore, 1 part by weight of tributylamine was blended with the compound obtained above, and the blend was then poured into a mold comprising 2 glass plates having an adjusted thickness of 2 mm. Afterward, the blend was polymerized/cured at 80° C. for 5 hours to obtain an optical material. The refractive index, the Abbe's number and the specific gravity of the thus obtained optical material were measured, and the results are shown in Table 2.

EXAMPLE 7

[in the general formula (II), v=0 (x=1, y=1, z=1 and u=1)]

The same procedure as in Example 6 was repeated except that 2-(2-mercaptoethylthio)-1,3-dimercaptopropane was replaced with 1,2-bis[(2-mercaptoethyl)thio]-3-dimercaptopropane, thereby obtaining 1,2-bis[(2-β-epithiopropylthioethyl)thio]-3-(β-epithiopropylthio)

propane in a total yield of 86%.

| Elemental analysis: | | Found | Calcd. |
| --- | --- | --- | --- |
| | C | 40.12% | 40.29% |
| | H | 6.09% | 5.92% |
| | S | 53.64% | 53.79% |

Mass spectrum (EI): M$^+$ 476 (theoretical molecular weight=476)

Infrared absorption spectrum: 620 cm$^{-1}$ (stretching vibration of an episulfide ring)

$^1$H-NMR:

2.2 ppm (hydrogen atoms bonded to carbon atoms at 1-, 16-, and 14'-positions)

2.6–3.1 ppm (hydrogen atoms bonded to carbon atoms at other positions)

$^{13}$C-NMR:

25.7 ppm (carbon atoms at 1-, 16- and 14'-positions)
30.0 ppm (a carbon atom at 6-position)
32.4 ppm (carbon atoms at 2-, 15- and 13'-positions)
32.5 ppm (a carbon atom at 11-position)
34.0 ppm (a carbon atom at 12-position)
34.5 ppm (a carbon atom at 5-position)
37.1 ppm (a carbon atom at 9-position)
37.3 ppm (a carbon atom at 9'-position)
38.4 ppm (carbon atoms at 3-, 14- and 12'-positions)
46.0 ppm (a carbon atom at 8-position)

After polymerization/curing, the refractive index, the Abbe's number and the specific gravity of the obtained optical material were measured, and the results are shown in Table 2.

EXAMPLE 8

[in the general formula (II), x=0, y=4, z=0 and u=0]

The same procedure as in Example 6 was repeated except that 2-(2-mercaptoethylthio)-1,3-dimercaptopropane was replaced with tetrakis(mercaptomethyl)methane, thereby obtaining tetrakis(β-epithiopropylthiomethyl)methane in a total yield of 78%.

| Elemental analysis: | | Found | Calcd. |
| --- | --- | --- | --- |
| | C | 41.59% | 41.76% |
| | H | 5.91% | 5.77% |
| | S | 52.30% | 52.47% |

Mass spectrum (EI): M$^+$ 488 (theoretical molecular weight=488)

Infrared absorption spectrum: 620 cm$^{-1}$ (stretching vibration of an episulfide ring)

$^1$H-NMR:

2.2 ppm (hydrogen atoms bonded to carbon atoms at 1-, 11-, 11'- and 11"-positions)

2.6 ppm (hydrogen atoms bonded to carbon atoms at 1-, 5-, 7-, 11-, 7'-, 11'-, 7"- and 11"-positions)

2.7 ppm (hydrogen atoms bonded to carbon atoms at 2-, 10-, 10'- and 10"-positions)

3.0 ppm (hydrogen atoms bonded to carbon atoms at 3-, 9-, 9'- and 9"-positions)

3.1 ppm (hydrogen atoms bonded to carbon atoms at 3-, 9-, 9'- and 9"-positions)

$^{13}$C-NMR:

25.7 ppm (carbon atoms at 1-, 11-, 11'- and 11"-positions)
32.5 ppm (carbon atoms at 2-, 10-, 10'- and 10"-positions)
37.3 ppm (carbon atoms at 5-, 7-, 7'- and 7"-positions)
38.5 ppm (a carbon atom at 6-position)
39.1 ppm (carbon atoms at 3-, 9-, 9'- and 9"-positions)

After polymerization/curing, the refractive index, the Abbe's number and the specific gravity of the obtained optical material were measured, and the results are shown in Table 2.

EXAMPLE 9

[in the general formula (II), v=2 (x=1, y=3, z=0 and u=0)]

The same procedure as in Example 6 was repeated except that 2-(2-mercaptoethylthio)-1,3-dimercaptopropane was replaced with 1,1,1-tris(mercaptomethyl)propane, thereby obtaining 1,1,1-tris(β-epithiopropylthiomethyl)propane (in the general formula (II), m=2 and v=2) in a total yield of 75%.

| Elemental analysis: | | Found | Calcd. |
| --- | --- | --- | --- |
| | C | 45.00% | 45.18% |
| | H | 6.67% | 6.57% |
| | S | 48.09% | 48.25% |

Mass spectrum (EI): M$^+$ 398 (theoretical molecular weight=398)

Infrared absorption spectrum: 620 cm$^{-1}$ (stretching vibration of an episulfide ring)

$^1$H-NMR:

1.0 ppm (hydrogen atoms bonded to a carbon atom at 8"-position)

1.5 ppm (hydrogen atoms bonded to a carbon atom at 7"-position)

2.2 ppm (hydrogen atoms bonded to carbon atoms at 1-, 11- and 11'-positions)

2.6-2.8 ppm (hydrogen atoms bonded to carbon atoms at 1-, 2-, 5-, 7-, 10-, 11-, 7'-, 10'- and 11'-positions)

3.0 ppm (hydrogen atoms bonded to carbon atoms at 3-, 9- and 9'-positions)

3.1 ppm (hydrogen atoms bonded to carbon atoms at 3-, 9- and 9'-positions)

$^{13}$C-NMR:

11.4 ppm (a carbon atom at 8"-position)
25.7 ppm (carbon atoms at 1-, 11- and 11'-positions)
28.5 ppm (a carbon atom at 7"-position)
32.4 ppm (carbon atoms at 2-, 10- and 10'-positions)
37.9 ppm (carbon atoms at 5-, 7- and 7'-positions)
38.8 ppm (a carbon atom at 6-position)
39.1 ppm (carbon atoms at 3-, 9- and 9'-positions)

After polymerization/curing, the refractive index, the Abbe's number and the specific gravity of the obtained optical material were measured, and the results are shown in Table 2.

Comparative Example 5

A mixture of 0.2 mol of 2-(2-mercaptoethylthio)-1,3-dimercaptopropane and 0.3 mol of metaxylylene diisocyanate was polymerized/cured. The refractive index, the Abbe's number and the specific gravity of the obtained material were measured, and the results are shown in Table 2.

Comparative Example 6

The same procedure as in Example 6 was repeated except that thiourea was used in an amount of 0.8 mol per mol of 2-(2-glycidylthioethylthio)-1,3-bis(glycidylthio)propane. It was apparent from an NMR spectrum that an obtained product had the general formula (II) of v=0, x=1, y=2, z=0 and u=1, and the ratio of S in X was 30% of the total of S and O constituting a three-membered ring on the average.

After polymerization/curing, the refractive index, the Abbe's number and the specific gravity of an obtained material were measured, and the results are shown in Table 2.

TABLE 2

| | Episulfide Compound | $N_D$ | $v_D$ | Specific Gravity | Heat Resistance | Strength |
|---|---|---|---|---|---|---|
| Example 6 | 2-(2-β-epithio-propylthioethyl-thio)-1,3-bis-(β-epithiopropyl-thio)propane | 1.69 | 36 | 1.38 | ○ | ○ |
| Example 7 | 1,2-bis[(2-β-epithio-propylthioethyl)-thio]-3-(β-epithio-propythio)propane | 1.70 | 36 | 1.38 | ○ | ○ |
| Example 8 | Tetrakis(β-epithio-propylthioethyl) methane | 1.69 | 36 | 1.37 | ○ | ○ |
| Example 9 | 1,1,1-tris(β-epithiopropylthio-methyl)propane | 1.68 | 37 | 1.35 | ○ | ○ |
| Comp. Ex. 5 | 0.2 mol of 2-(2-mercaptoethyl-thio)-1,3-dimer-captopropane and 0.3 mol of meta-xylylene diiso-cyanate | 1.66 | 32 | 1.37 | X | ○ |
| Comp. Ex. 6 | In general formula (II) of v = 0, x = 1, y = 2, z = 0 and u = 1, ratio of S in X was 30% of total of S and O on the average. | 1.62 | 38 | 1.29 | Δ | Δ |

A novel alkyl sulfide type episulfide compound of the present invention enables the provision of a resinous optical material having a sufficiently high refractive index and a good balance between the refractive index and an Abbe's number which can scarcely be attained by using conventional compounds as materials. In addition, the present invention can provide a resinous optical material having the good balance between the refractive index and the Abbe's number as well as a high heat resistance. In particular, a branched alkyl sulfide type episulfide compound represented by the general formula (II) enables the provision of a resinous optical material having a very high heat resistance.

That is to say, the employment of the novel compound of the present invention can noticeably advance the lightening and the thinning of the resinous optical material as well as the reduction of chromatic aberration. In addition, the reduction in the weight and the thinning of the resinous optical material as well as the reduction of chromatic aberration are also possible, while the high heat resistance is maintained.

Furthermore, an optical material obtained by polymerizing/curing the novel alkyl sulfide type episulfide compound of the present invention can be used for various purposes, and it is particularly desirable as a lens material for spectacles.

What is claimed is:

1. An alkyl sulfide type episulfide compound represented by the formula (I) or (II)

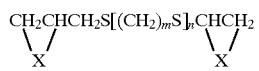
(I)

-continued

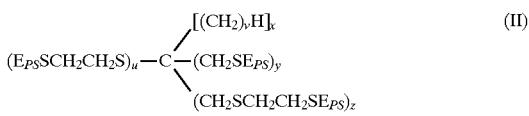
(II)

in the formula (I), m is an integer of 1 to 6; n is an integer of 0 to 4; each X is S or O, and the ratio of S is independently, on the average, 50% or more of the total of S and O constituting a three-membered ring; and in the formula (II), x is an integer of 0 to 1; y is an integer of 0 to 4; z is an integer of 0 to 4; u is an integer of 0 to 1; v is an integer of 0 to 3; the relation of x+y+z+u=4 is met; and $E_{ps}$ is a

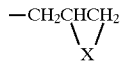

group, wherein X is the same as X in the formula (I).

2. The alkyl sulfide type episulfide compound according to claim 1 which is represented by

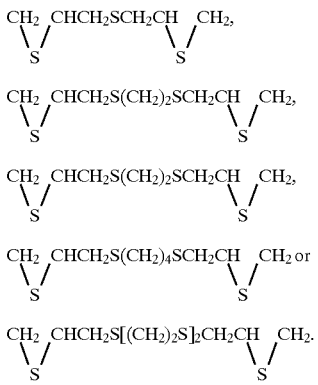

3. The alkyl sulfide type episulfide compound according to claim 1 which is represented by $C(CH_2SE_{PS})_4$, $E_{ps}SCH_2CH_2SCHCH_2SE_{ps}$,
  |
  $CH_2SE_{ps}$ $E_{ps}SCH_2CH_2SCHCH_2SE_{ps}$,
  |
  $CH_2SCH_2CH_2SE_{ps}$ or
$CH_2C(CH_2SE_{PS})_3$ $CH_3CH_2C(CH_2SE_{PS})_2$, wherein $E_{ps}$ is

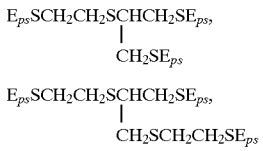

wherein X is S or O.

4. An optical material which is obtained by polymerizing and curing an alkyl sulfide type episulfide compound described in any one of claim 1.

5. An optical material which is obtained by polymerizing and curing an alkyl sulfide type episulfide compound described in claim 2.

6. An optical material which is obtained by polymerizing and curing an alkyl sulfide type episulfide compound described in claim 3.

7. The alkyl sulfide type episulfide compound according to claim 1, wherein n is 0 to 3, and m is 2 to 4.

8. The alkyl sulfide type episultide compound according to claim 1, wherein n is 0 to 2, and n is 2 to 3.

9. The alkyl sulfide type episulfide compound according to claim 1, which is selected from the group consisting of

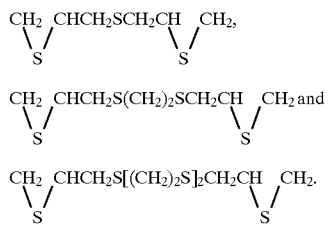

10. The alkyl sulfide type episulfide compound according to claim 1, wherein the compound is of the formula (I).

11. The alkyl sulfide type episulfide compound according to claim 1, wherein the compound is of the formula (II).

12. The alkyl sulfide type episulfide compound according to claim 1, wherein each X in the formula (I) is a sulfur atom.

13. The alkyl sulfide type episulfide compound according to claim 1, wherein the ratio is 80 to 100%.

14. The alkyl sulfide type episulfide compound according to claim 1, wherein the ratio is 90 to 100%.

15. The alkyl sulfide type episulfide compound according to claim 1, wherein the ratio is 95 to 100%.

* * * * *